United States Patent [19]

Smith et al.

[11] Patent Number: 5,759,860
[45] Date of Patent: Jun. 2, 1998

[54] AUTOMATED ANALYSIS METHOD FOR DETECTING BACTERIAL NITRITE IN URINE

[75] Inventors: Jack V. Smith, St. Petersburg; Jesse M. Carter, Tampa, both of Fla.

[73] Assignee: Chimera Research & Chemical, Inc., Largo, Fla.

[21] Appl. No.: 618,499

[22] Filed: Mar. 19, 1996

Related U.S. Application Data

[63] Continuation-in-part of Ser. No. 429,292, Apr. 24, 1995, Pat. No. 5,516,700, which is a continuation-in-part of Ser. No. 68,956, May 28, 1993, abandoned.

[51] Int. Cl.$^6$ .................. G01N 33/493; G01N 31/22
[52] U.S. Cl. .................................. 436/110; 436/164
[58] Field of Search .................. 436/106, 110, 436/164

[56] References Cited

U.S. PATENT DOCUMENTS

| | | | |
|---|---|---|---|
| 3,718,543 | 2/1973 | Lagomarsino | 435/37 |
| 3,992,158 | 11/1976 | Przybylowicz et al. | 422/56 |
| 4,061,468 | 12/1977 | Lange et al. | 422/56 |
| 4,517,301 | 5/1985 | Greene | 422/56 |
| 4,934,235 | 6/1990 | Rabi et al. | 436/110 |
| 5,516,700 | 5/1996 | Smith et al. | 436/164 |

*Primary Examiner*—Lyle A. Alexander
*Attorney, Agent, or Firm*—Larson & Larson, P.A.; James E. Larson

[57] ABSTRACT

Placing an aliquot of a urine sample in an automated analyzer first sampling cup, and a standard containing a known quantity of nitrite in a second cup. Injecting known specified amounts of each sample from these cups into discrete cuvettes in the autoanalyzer, injecting at least one reagent composition in an aqueous medium containing a buffer, a compound to remove substances in the urine interfering with a colorimetric reaction, oxidized glutathione, and B-nicotinamide adenine dinucleotide phosphate or nicotinamide adenine dinucleotide and reading at a preprogrammed code in an automated analyzer at a preprogrammed wavelength to compare the patient's urine with the standard to determine quantitatively the presence of bacterial nitrite in the patient's urine.

6 Claims, No Drawings

AUTOMATED ANALYSIS METHOD FOR DETECTING BACTERIAL NITRITE IN URINE

Prior Applications

This application is a continuation-in-part of application Ser. No. 08/429,292, filed Apr. 24, 1995, now U.S. Pat. No. 5,516,200 which is a continuation-in-part of application Ser. No. 08/068,956, filed May 28, 1993, (now abandoned).

BACKGROUND OF THE INVENTION

This invention relates to a method and materials that are designed for use in automating urinalysis. This system is designed to analyze urine for its constituents by a method that is fully automated (does not require the use of manual methods such as refractometer, pH meter, dipsticks, or impregnated test strips. Automation as designed by this system is directed to the use of a self-operating instrument that is capable of handling multiple reagents designed for use on an automated analyzer system for the quantitative determination of Bacterial Nitrite.

It is known that the most common method for the analysis of urine is by the use of a manual technique known as a dipstick. This method for the analysis of urine is labor, time intensive, and costly among other detriments. The use of a dipstick for analysis of urine also relies on the subjective interpretation of the technician. The dipstick method requires the technician to submerge the dipstick in a sample of urine and remove it, wait a specified time, then compare the color development of the test on the dipstick to a color chart. Even more cumbersome methods involve the use of a refractometer, pH meter, or manual chemistry test.

The following list of assay devices utilizing prior art includes dry tablets, dipsticks, or impregnated test strips for the analysis of urinary constituents. None of the prior devices foresee or teach a multiple/single liquid reagent system designed specifically for auto-analyzers to analyze urinary constituents quantitatively.

One such U.S. Pat. No. 4,147,514 discloses test strips (dipsticks) for the detection of ketone bodies. The assay strips are made up of a chemical bonded to a cellulose pad on a strip. This is then dipped into a specimen sample. This method only determines ketone bodies qualitatively at its best, due to inability of the system to allow the use of standards and controls on the same strip to which the sample is applied.

Another such patent, U.S. Pat. No. 3,146,070 discloses analytical compositions in dry form on a bibulous carrier (dipstick) impregnated with a pH indicator for the determination of pH. This assay at best only determines pH qualitatively, due to the inability to use standards and controls located on the same strip for the same test sample to define and verify a quantitative determination.

Additionally, U.S. Pat. No. 4,318,709 discloses a device comprising a carrier matrix (dipstick) impregnated with the test means for specific gravity. This assay at best only determines specific gravity qualitatively, due to the inability to use standards and controls located on the same strip for the same test specimen. The prior art in this case also did not foresee the wide specimen to specimen matrix variations of real world urine samples including matrix components such as pH, and ionic strength, and the concomitant requirement of a multiple reagent system to effectively analyze urine for specific gravity in a liquid to liquid reaction. The normal pH value for urine can range from 4.5 to 8.0, which if using the prior dipstick method the results would be widely scattered and inaccurate without a reagent component to neutralize this effect prior to completion of the assay.

Various devices are described in the literature for the determination of particular urinary constituents one by one with the use of carrier matrices (dipstick, microcapsules, filter paper, etc.). None of the prior art teaches or elucidates a means for determining by automated technology urinary constituents from a single sample of urine, via multiple tests that are reported simultaneously by an autoanalyzer using liquid reagents specifically designed for this family of instruments. As cited by the prior art, (in package insert literature) when evaluating laboratory test results, definitive diagnostic, or therapeutic decisions should not be based on any single result or method. However, the prior art states that dipsticks are affected by high specific gravity, substances that cause abnormal urine color, such as drugs containing azo dyes (e.g., Pyridium, Azo Gantrisin, Phenazopyridyine) and ascorbic acid and thus may affect the readability of reagent areas on the urinalysis reagent strips (dipsticks). The color development on the reagent pad may be masked, or a color reaction may be produced on the pad that could be interpreted visually and/or instrumentally as a false positive or negative.

SUMMARY OF THE INVENTION

The automated urinalysis system of this invention offers a method for reducing the consumable materials and labor costs. The system also offers increased accuracy, sensitivity, and objective quantifiable determinations of urinary constituents for better diagnostic interpretation of the test results of urine, thus enabling a physician to provide better health care for the patient.

This invention satisfied many of the problems unanswered by the prior art: quantitative results, non-subjective results, reproducible results, increased accuracy, precision, sensitivity, carrier free reagents, reagents designed for autoanalyzer use, reagents uniquely designed for each particular urine analyte assay overcoming matrix problems previously unanswered by prior art, a method allowing vast improvement of test completion time (hundreds to thousands per hour). The present invention presents a fully automateable walk-away urinalysis system applicable to any discrete autoanalyzer currently in use, and obviously represents a marked advancement in the art of urinalysis. The clear cut object of the present invention is to provide a more comprehensive method for determining urinary constituents of Bacterial Nitrite, such method specifically yielding improved health care.

Thus, it is a primary objective of the present invention to provide techniques for determination of urinary constituents of Bacterial Nitrite activity at low chemically significant levels.

An additional object of this invention is to make available an advanced method for analyzing a sample of urine for the quantitation of its constituents on an autoanalyzer. The advanced ability of the automated urinalysis system to offer a means for automated analysis on urine is a significant improvement in the art of urinalysis.

Additionally, the object of this invention is to provide a comprehensive method which is broadly adaptable to a wide variety of automated analyzers presently in use in the industry which will increase accuracy, sensitivity, precision, and speed. An autoanalyzer allows for precise quantitative results beyond the scope and abilities of the prior art. An autoanalyzer, used in conjunction with the automated urinalysis reagents used in this invention, provides a system that produces an objective quantitative result of an unknown urine sample obtained from a linear standard curve determined by analysis of standards run on the instrument, and verified as accurate by quantifying controls of known value. This simultaneous analysis of standards, controls and unknowns (urine samples) yielding unbiased results improves the art of urinalysis significantly over the prior art, which yields only qualitative and subjective results.

It is a further object of this invention to provide a method for the simultaneous determination of multiple urinary components of Bacterial Nitrite activity, from a single urine sample using a system of reagents designed for autoanalyzer use. This improvement in the science of urinalysis over the prior art proves to be significant medically and economically.

Another object of this invention is to provide a method that yields quantifiable results in the determination of urinary constituents present in a sample of urine.

Still another object of this invention is to provide a method for the determination of objective results (from the photometric analysis by the automated analyzer) instead of the subjective determination (from human observation). The present invention provides a unique formulated reagent system that can be mixed with unknown urine samples, standards, and controls and then be read spectrophotometrically with unbiased accuracy on an autoanalyzer. The use of the automated urinalysis system provides a means for improved accuracy, precision, and specificity by removal of the subjective human element from the analysis. Clearly, a system that automatically dispenses, measures, and records results is a marked improvement in the science of urinalysis.

Yet another object of this invention is to provide uniquely formulated reagents for each urinalysis assay that were not taught or envisioned by the prior art, and overcome the inadequacies of the prior art. Consider the fact that one of the primary means of optimizing enzymic assays is identifying the best temperature, and performing the assay at that temperature. The prior art can only be used at room temperature which can vary over a wide range from test location to location, and from day to day in the same facility. Such variation adds to the imprecision, insensitivity, and inaccuracy of the prior art. Conversely, the present invention is compatible with current autoanalyzers which precisely control temperature of the reaction cuvettes as prescribed by the as say parameters. Thus, this invention's enzyme-based and nonenzyme-based assays can be optimized for temperature thereby obtaining consistent results with even greater sensitivity, precision, and accuracy then previously possible.

Yet another object of this invention is to provide uniquely formulated reagents for each urinalysis assay that were not taught or envisioned by the prior art, and overcome the inadequacies of the prior art. Consider the fact that urea is the largest component of urine (besides water) by a factor of 50% over the next largest component (sodium chloride). A unique chemical formulation to compensate for urea is an advancement in the art of urinalysis. The present invention is a liquid reagent that is not carrier dependent, designed for autoanalysis, and has agents added to remove the urea and other interfering ions from the solution, thus preventing it from interacting with the color developer. These improvements increase sensitivity, accuracy, and precision, thereby allowing the measurement of Bacterial Nitrite assay in urine to be quantifiable.

Yet another object of this invention is to provide uniquely formulated reagents for each automated urinalysis assay that was not taught or envisioned by the prior art. The assay for Bacterial Nitrite activity, in the prior art has limited application and accuracy because it is carrier dependent, and it only produces qualitative results (i.e., positive or negative with a range of 0.06 to 0.1 mg/dl of nitrite ions present). The measurement of nitrite is an indirect method suggesting the presence of gram negative micro organisms that reduce nitrate to nitrite. Urinary tract infections can occur from organisms that do not convert nitrate to nitrite (i.e., gram positive bacteria), thus a false negative would occur. If dietary nitrate were absent, the gram negative bacteria could not make nitrite, again resulting in a false negative test. If the urine is not held in the bladder for at least 4 hours, a false negative can again result because the bacteria require this time to convert nitrate to nitrite in sufficient quantities for detection. It should be noted that frequent urination is often associated with bacterial urinary infection. The prior method yields a non-specific color development for determination of Nitrite present making objective and monochromatic spectrophotometric analysis difficult. Extrapolation of prior art to the present invention is not readily apparent to anyone schooled in the art of urinalysis. The prior art is susceptible to interferences from sample matrices including, but not limited to those with a high ionic strength, vitamin C and Azo drugs such as phenazopyridyine. The present invention is a liquid reagent that is not carrier dependent, and is specifically designed for use on autoanalyzers. The present invention is quantitatively linear from 0.05 mg/dl to 1.0 mg/dl nitrite ions present. The present invention also directly measures quantitatively the amount of reductase present (which is the enzyme present that converts nitrate to nitrite). There are several advantages to measuring the reductase including, but not limited to more direct measurement of bacteria present, bladder incubation time not required, and resulting assay is more accurate, sensitive, and quantitative. The present invention utilizes colorimetric reagents specifically designed for autoanalyzer, and can directly measure the amount of nitrite ion, or reductase present. The present invention has a compensator for the pH of the random urine sample which can range from 4.5 to 8.0. It should be noted that nitrate reductase activity is optimal at a pH of 6.8. Buffering the sample to this pH is critical to obtaining optimal sensitivity, accuracy, and precision. The present invention measures the activity of nitrate reductase on nitrate (substrate) by the disappearance of nicotinamide adenine dinucleotide phosphate (NADPH) which absorbance can be monitored at 340 nm. The prior art has no means to compensate for abnormal pH, resulting in poor sensitivity and selectivity of the assay. The present invention has curve stabilizers and agents to compensate for a variety of interfering substances found in urine, which the prior art did not teach or envision. The present invention is quantitative, carrier independent, precise, accurate, automateable, and sensitive, and represents an obvious advancement in the art of urinalysis.

DETAILED DESCRIPTION OF THE INVENTION

The presently claimed method comprises a group of carrier-free liquid reagents designed for simultaneous usage on automated analyzers for quantitative determination of urinary constituents. The automated urinalysis system of the instant invention solves the problems confronting automating the analysis of urine, and in the process, represents a significant improvement over the present art. These improvements which facilitate application to automation and represent significant technical improvement over the previous art include, a buffering system for pH variation in urine by correcting pH to the analytically preferred value prior to analysis and also stabilizing reaction rates thereby improving linearity and neutralizing the interference effects of the highly complex matrix of random urines submitted for analysis. Additional technical improvement is due to the addition of components to remove interfering substances yielding reduced assay limitations and increased linearity, accuracy and precision in the resulting quantitations. These unique reagent formulations allow automation resulting in, but not limited to, enhanced speed, objectivity, accuracy and sensitivity associated with the automated test. A synopsis of the automated testing process follows. The entire automated urinalysis reagent system is loaded into an autoanalyzer. The controls, standards and unknown urine samples are fed into the autoanalyzer sampling cups, individually mixed with each test reagent in discrete cuvettes, the absorbance read and quantitation determined for comparison with the standard curve.

The composition of each reagent of the present invention is designed for optimum reaction with the random urine samples and to effectively deal with problems arising from the tremendous variability from sample to sample due to the diet, disease state, medications, time of collection, state of hydration, sex, age and physical well being of the patient. All of the factors can interfere with the prior art test procedures.

The automated urinalysis system reagents are individually designed for optimum analysis of specific urinary components. The reagent system for Bacterial Reductase/Nitrite/Indole activity (as a measure for bacterial uremia) in urine is carrier independent and has specific agents added to compensate for interference from enzyme inhibitors and other abnormal amounts of urinary constituents. The reagent system is composed of two reagents, but can consist of one reagent. The first reagent (R1), is specifically designed to neutralize matrix interference and increase sample to liquid reagent compatibility with the autoanalyzer. The component, 2,3-butanedione monoxime is included in this first reagent (R1) to remove urea and other substances found in urine that cause interference with the colorimetric reaction. Ethylenediaminetetraacetic acid and dimercaptopropanol are other components of the R1 that neutralize interfering substances by chelation, inactivation of enzyme inhibitors and anti-oxidant activity. These compounds remove oxidizing contaminants such as hypochlorite and act as solution clarifiers (i.e., they absorb or cause the disappearance of the characteristic yellow color of urine), thereby enhancing spectrophotometric analysis. One of several analytical pathways utilizes oxidized glutathione (GSSG) to act as a substrate for the bacterial reductase. B-Nicotinamide Adenine Dinucleotide Phosphate (NADPH) and/or Nicotinamide Adenine Dinucleotide (NADH) are present to act as coenzymes for the reductase enzyme reaction. Utilizing another analytical pathway the R1 contains the above referenced components to neutralize sample matrix interference and one or more of the following: Sulfuric acid, hydrochloric acid, Phosphoric acid, p-Arsanilic acid, Sulfanilamide, N-Sulfanilylsulfanilamide and/or sodium iodide (or other salt forms). The R1 also contains a buffer to adjust sample pH, aid in solubility and compatibility of the reagent's complex chemical matrix. This complex chemical matrix requires a complementary aqueous buffering system with unique dynamics capable of adjusting reaction solution to the ideal pKa and promoting reagent component solution compatibility with autoanalyzers. Unbuffered solutions may have high acidic or basic activity, or strictly organic properties which are not compatible with autoanalyzer syringes, tubing, metal and plastic parts. The buffer also promotes carrier independence. The R1 also contains surfactants that enhance the carrier free matrix, decrease surface tension, promote effective mixing on a molecular level and improve flow dynamics through tubing and syringes of automated analyzers. The R1 buffer constituents and concentrations can be varied to compensate for variations in the configuration of sampling and reagent delivery systems of various makes of autoanalyzers. The buffers also compensate for abnormal pH of urine and urines with high buffering capacities.

The Bacterial Reductase/Nitrite/Indole reagent system's second reagent (R2) is the color generating reagent of the two reagent set unless a single reagent system is used. This second reagent (R2) may utilize a reaction pathway that requires one or more of the following: GSSG, NADPH, NADH, or p-dimethyl-aminobenzaldehyde (DMABA) as an indicator for aerobic and anaerobic activity correlated to indole production. Utilizing another analytical pathway the R2 contains one or more of the following: a salt of iodide (Na, K, etc . . . ), N-(1-naphthyl) ethylenediamine, 1,2,3,4,-tetrahydroisoquinoline hydrochloric acid, 4-nitrobenzenediazonium tetrafluroborate, or another suitable azo dye that forms a complex with the diazonium salt, which can be measured spectrophotometrically at 540 nm. This second reagent (R2) can utilize a reaction pathway that requires one or more of the following: Triphenyltetrazolium chloride acts as a substrate for the bacterial reductase and when reduced, yields a colorimetrically measurable compound. In the presence of the NADH and/or NADPH reduced triphenyltetrazolium chloride will also yield a color reaction at 340 nanometers. The buffers are added to adjust sample pH, aid in solubility and compatibility of the reagent's complex chemical matrix. This complex chemical matrix requires a complementary aqueous buffering system with unique dynamics capable of adjusting the reaction solution to the ideal pKa and promoting reagent component solution compatibility with autoanalyzers. Unbuffered solutions may have high acidic and basic activity or strictly organic properties which are not compatible with autoanalyzer syringes, tubing, metal and plastic parts. The buffers also promote carrier independence. The R2 also contains surfactants that enhance the carrier free matrix, decrease surface tension, promote effective mixing on a molecular level and improve flow dynamics through tubing and syringes of automated analyzers. The preceding components and the concentrations of the components of the R1 and/or the R2 reagents can be varied to compensate for limitations, variations in the configuration of sampling and reagent delivery systems of various makes of autoanalyzers. The above constituents can be varied, to compensate for said differences. Without further elaboration, it is believed that one skilled in the art, using the preceding description, can effectively utilize the present invention. The following preferred specific embodiments are, therefore, to be construed as merely illustrative, and not limited to the remainder of the disclosure in any way whatsoever. In the following examples, all instrument parameters, reagent combinations and method techniques are set forth.

EXAMPLE 1

In the automated urinalysis system reagents for bacterial reductase assay, the first reagent (R1), contains surfactant, 2,3-butanedione monoxime, ethylenediaminetetraacetic acid (sodium salt), dimercaptopropanol and buffer. The second reagent R2 contains surf actant, buffer, GSSH, NADPH or NADH. The reagents are placed in the autoanalyzer. The urine sample, standards and controls are placed in the autoanalyzer specimen cups. The urine sample, standards and control are mixed with the first reagent in separate cuvettes. Then the second reagent is added and the solution is mixed and read at specified intervals as dictated by the instrument parameters and at the specified wavelength (monochromatically) depending on reagent combination used. In this instance, the assay is read at 340 nanometers and read times are specific to the analyzer. Analyzer temperature is set at 37 degrees C. NOTE: This example reagent determines reductase activity directly. No nitrite or incubation time is necessary.

EXAMPLE 2

In the automated urinalysis system reagent for bacterial reductase employing a dual reagent system, the first reagent (R1) contains ethylenediaminetetraacetic acid, buffers, sulfanilamide, hydrochloric acid (or another suitable acid), and surfactants. The R2 reagent contains hydrochloric acid, N-(1-naphthyl)ethylenediamine and/or 1,2,3,4,-tetrahydroisoquinoline hydrochloric acid, or 1,2,3,4-tetrahydrobenzoquinolin-3-ol (or other suitable azo dye). The reagents are placed in the autoanalyzer. The urine sample, standards and controls are placed in the autoanalyzer specimen cups. The urine sample, standards and control are mixed with the reagent in separate cuvettes and the solution is read at specified intervals as dictated by the instrument parameters and at the specified wavelength (monochromatically) depending on reagent combination used. In this instance, the assay is read at 540 nanometers wavelength and read times are specific to the analyzer. Analyzer temperature is set at 37 degrees C. NOTE: This example reagent determines reductase activity indirectly through production of Nitrite from Nitrate following sufficient incubation time.

EXAMPLE 3

In the automated urinalysis system reagents for bacterial reductase, the first reagent (R1) contains surfactants, buffer, 2,3-butanedione monoxime, ethylenediaminetetraacetic acid and dimercaptopropanol. The R2 second reagent contains p-arsanilic acid, 1,2,3,4-tetrahydrobenzoiquinolin-3-ol, buffers and surfactants. The reagents are placed in the autoanalyzer. The urine samples, standards and controls are placed in the autoanalyzer specimen cups. The urine samples, standards and controls are mixed with the first reagent in separate cuvettes. Then the second reagent is added and the solution is mixed, read at specified intervals as dictated by the instrument parameters and at the specified wavelength monochromatically depending on reagent combination used. In this instance, the assay is read at 540 nanometers and read times are specific to the analyzer. Analyzer temperature is set at 37 degrees C. NOTE: This example reagent determines reductase activity indirectly.

EXAMPLE 4

In the automated urinalysis system reagents for bacterial reductase in the single reagent system (R1), contains surfactant, NADH and/or NADPH, ethylenediaminetetraacetic acid, buffers, and GSSH. The reagents are placed in the autoanalyzer. The urine samples, standards and controls are placed in the autoanalyzer specimen cups. The urine samples, standards and controls are mixed with the first reagent in separate cuvettes, and read at specified intervals as dictated by the instrument parameters at the specified wavelength (monochromatically) depending on reagent combination used. In this instance the assay is read at 340 nanometers and read times are specific to the analyzer. Analyzer temperature is set at 37 degrees C. NOTE: This example reagent determines reductase activity directly, requiring no nitrate or incubation time.

EXAMPLE 5

In the automated urinalysis system reagents for bacterial reductase the first reagent (R1), contains surfactant, ethylenediaminetetraacetic acid (sodium salt), dimercaptopropanol and buffer. The second reagent R2 contains triphenyltetrazolium chloride, buffer and surfactant. The reagents are placed on the autoanalyzer. The urine samples, standards and controls are placed in the autoanalyzer specimen cups. The urine samples, standards and controls are mixed with the first reagent in separate cuvettes. Then the second reagent is added and the solution is mixed and read at specified intervals as dictated by the instrument parameters and at the specified wavelength (monochromatically) depending on reagent combination used. In this instance, the assay is read at 340 nanometers and read times are specific to the analyzer. NOTE: This example reagent determines reductase activity indirectly through production of nitrite from nitrate following sufficient incubation time.

EXAMPLE 6

In the automated urinalysis system reagents for bacterial reductase assay in the first reagent (R1) contains surfactant, 2,3-butanedione monoxime, and buffer. The second reagent R2 contains surfactant, buffer and p-dimethylaminobenzaldehyde (DMABA). The reagents are placed in the autoanalyzer. The urine sample, standards and controls are placed in the autoanalyzer specimen cups. The urine samples, standards and control are mixed with the first reagent in separate cuvettes. Then the second reagent is added and the solution is mixed and read at specified intervals as dictated by the instrument parameters and at the specified wavelength (monochromatically) depending on reagent combination used. In this instance, the assay is read at 540 nanometers and read times are specific to the analyzer. NOTE: this example reagent determines reductose activity indirectly through production of nitrite from nitrate following sufficient incubation time.

From the foregoing, it is believed that those familiar with the art will readily recognize and appreciate the novel concepts and features of the present invention. Numerous variations, changes and substitutions of equivalents will present themselves from persons skilled in the art and may be made without necessarily departing from the scope and principles of this invention. Therefore, the invention has been described with reference to a number of its embodiment, it can nevertheless be arbitrarily varied within the scope of the following claims.

What is claimed is:

1. An automated method for detecting bacterial nitrite in a patient's urine sample without employing an impregnated test strip, the steps comprising placing an aliquot of the urine to be tested in a first automated analyzer sampling cup, placing a standard containing a known concentration of bacterial nitrite in a second automated analyzer sampling cup, placing the cups in a sampling tray within the automated analyzer, transferring the urine from the first sampling cup to a cuvette mounted within the automated analyzer, injecting a first and second reagent composition in an aqueous medium into the cuvette, wherein said first reagent composition comprises a buffer to adjust the pH of the urine to a preferred value, a compound to remove substances in the urine interfering with a colorimetric reaction selected from the group consisting of ethylenediaminetetraacetic acid, dimercaptopropanol and 2,3-butanedione monoxime, together with a nitrite co-indicator compound selected from the group consisting of p-dimethylaminobenzaldehyde, triphenyltetrozolium chloride, sulfanilaiide, and p-arsanilic acid and the second reagent composition comprising a buffer, or mineral acid, a surfactant, and a nitrite indicator compound selected from the group consisting of N-(1-naphthyl)ethylene diamine and 3-hydroxy-1,2,3,4, tetra-hydro-7,8 benzoquinoline, reading at specified intervals, in accordance with a preprogrammed code introduced into the automated analyzer, at a preprogrammed monochromatically specified wavelength, to compare absorbance of the patient's urine and reagent composition complex with that of the standard and thereby determining quantitatively the presence of bacterial nitrite in the patient's urine.

2. The method according to claim 1 wherein the wavelength of the analyzer is about 340 nanometers.

3. The method according to claim 1 wherein the wavelength of the analyzer is about 540 nanometers.

4. The method according to claim 1 wherein the wavelength of the analyzer is about 600 nanometers.

5. The method according to claim 1 wherein the urine sample is buffered to adjust the pH of the urine to 6.8.

6. The method according to claim 1 wherein the wavelength of the analyzer is a single wavelength between about 340 nanometers and 800 nanometers.

* * * * *

UNITED STATES PATENT AND TRADEMARK OFFICE
CERTIFICATE OF CORRECTION

PATENT NO. : 5,759,860
DATED : June 2, 1998
INVENTOR(S) : Jack V. Smith et al.

It is certified that error appears in the above-identified patent and that said Letters Patent is hereby corrected as shown below:

Title page,
Item [63]; Related U.S. Application Data,
Please delete "continuation-in-part of Ser. No. 68,956" and insert -- continuation of Ser. No. 68,956 --.

Column 1,
Line 9, please delete "continuation-in-part" and insert -- continuation --.

Signed and Sealed this

Twenty-seventh Day of November, 2001

Attest:

NICHOLAS P. GODICI
*Attesting Officer*   *Acting Director of the United States Patent and Trademark Office*